United States Patent [19]

Harandi et al.

[11] Patent Number: 4,981,491

[45] Date of Patent: * Jan. 1, 1991

[54] PRODUCTION OF ETHER-RICH FUEL

[75] Inventors: Mohsen N. Harandi, Lawrenceville; Hartley Owen, Belle Mead, both of N.J.

[73] Assignee: Mobil Oil Corporation, New York, N.Y.

[*] Notice: The portion of the term of this patent subsequent to May 2, 2006 has been disclaimed.

[21] Appl. No.: 386,178

[22] Filed: Jul. 28, 1989

[51] Int. Cl.$^5$ ............................................... C10L 1/18
[52] U.S. Cl. ...................................... 44/448; 44/449; 568/697
[58] Field of Search ................ 44/77, 53, 56; 585/310

[56] References Cited

U.S. PATENT DOCUMENTS

| | | | |
|---|---|---|---|
| 4,191,846 | 3/1980 | Farah et al. | 585/440 |
| 4,193,770 | 3/1980 | Chase et al. | 44/56 |
| 4,252,541 | 2/1981 | Herbstman | 44/56 |
| 4,329,516 | 5/1982 | Al-Muddarris | 568/697 |
| 4,377,393 | 3/1983 | Schleppinghoff | 44/63 |
| 4,413,150 | 11/1983 | Briggs | 568/697 |
| 4,826,507 | 5/1989 | Harandi et al. | 44/77 |
| 4,827,046 | 5/1989 | Harandi | 568/697 |
| 4,830,635 | 5/1989 | Harandi et al. | 44/56 |

*Primary Examiner*—Olik Chaudhuri
*Assistant Examiner*—Ellen McAvoy
*Attorney, Agent, or Firm*—Alexander J. McKillop; Charles J. Speciale; L. G. Wise

[57] ABSTRACT

Methanol or other alcohol is converted to high octane gasoline components by an integrated process wherein crude aqueous alcohol feedstock is extracted with a liquid extractant stream containing $C_4^+$ iso-olefin and reacted to form tertiary-alkyl ethers, such as MTBE. The aqueous raffinate is converted to predominantly gasoline range liquid hydrocarbons in a MTG catalytic reactor, with byproduct alkanes rich in propane and isobutane. Dehydrogenation of $C_3$-$C_5$ alkanes from the MTG unit provides propene and isobutene reactants for subsequent etherification steps. Propene from the MTG dehydrogenation step is reacted with water to produce di-isopropyl ether, which may be blended with MTBE and $C_6^+$ MTG hydrocarbons to produce high octane gasoline. Isobutylene and isoamylenes from the MTG dehydrogenation step can be removed and recycled as a liquid extractant stream.

23 Claims, 1 Drawing Sheet

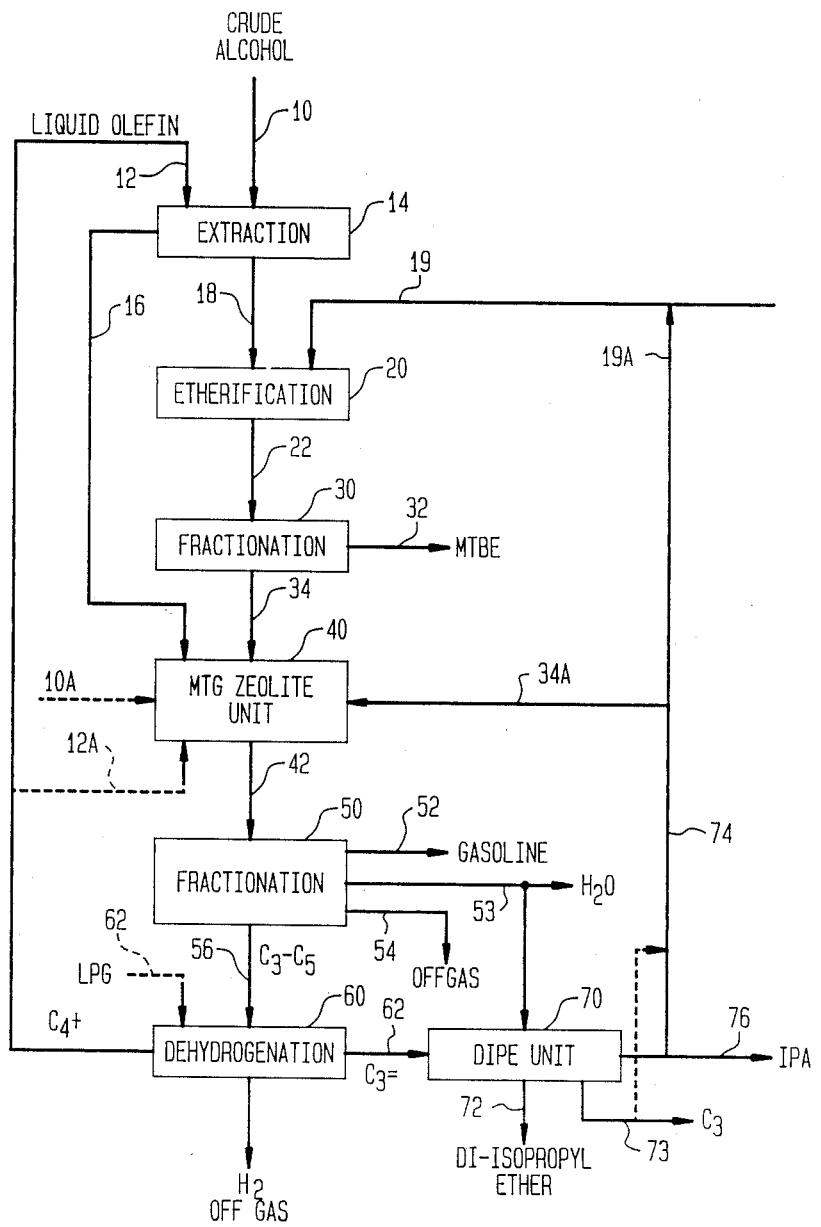

PRODUCTION OF ETHER-RICH FUEL

BACKGROUND OF THE INVENTION

This invention relates to techniques for converting crude methanol or other $C_1$–$C_4$ lower aliphatic alcohols to alkyl tertiary-alkyl ethers, di-isopropyl ether (DIPE), and gasoline range hydrocarbons. In particular, this invention relates to an improvement in utilizing methanol-to-gasoline (MTG) processes and operating synfuel systems for converting crude methanol to valuable products by etherifying lower olefins, such as $C_3$–$C_5$ olefins. Methanol is considered the most important oxygenate feedstock because of its widespread availability and low cost. In view of the predominant supply of methanol feedstock, the invention will be discussed primarily with this material as an example; however, it is understood that other lower aliphatic oxygenated hydrocarbons may be employed as the main feedstock or auxiliary streams.

Technical progress of the commercial MTG process has provided an important synthetic fuel source. Also, there has been recent independent development of processes for making alkyl tertiary-alkyl ethers as octane boosters in place of conventional lead additives in gasoline. The etherification processes for the production of methyl tertiary-alkyl ethers, in particular methyl t-butyl ether (MTBE) and t-amyl methyl ether (TAME) have been the focus of considerable research. Recognizing the common feedstock (e.g.—methanol) for the synthetic production of gasoline as well as the production of methyl t-alkyl octane boosting ethers, research workers have endeavored to combine these processes in a manner to provide a synergistically beneficial integrated process. Increasing demand for high octane gasolines blended with lower aliphatic alkyl ethers as octane boosters and supplementary fuels has created a significant demand for isoalkylethers, especially the $C_5$ to $C_7$ methyl, ethyl and/or isopropyl t-alkyl ethers, such as methyl t-butyl ether (MTBE). It is known that feedstock dewatering and recovering unreacted methanol by conventional separation and extraction techniques imposes severe economic burdens on the etherification process. Crude methanol usually contains a significant amount of water, typically in the range of 2 to 20 wt %; however, the present invention is useful for removing water in lesser amounts or greater.

It is main object of the present invention to provide a novel and economic technique for removing excess water from crude methanol feedstocks, including novel operating methods and equipment for treating these oxygenate feedstocks prior to etherification and disposing of raffinate containing methanol. It has been discovered that aqueous methanol streams, such as etherification feedstock extraction byproduct can be economically upgraded by catalytic conversion concurrently with hydrocarbons.

SUMMARY OF THE INVENTION

A continuous technique has been found for converting crude methanol or the like to high octane gasoline and mixed ethers. An improved MTG process is provided for converting crude aqueous alcohol feedstock to liquid fuel rich in alkyl ethers comprising the steps of: contacting a crude methanolic feedstock containing water with a liquid olefinic hydrocarbon extraction solvent stream rich in $C_4^+$ iso-alkene hydrocarbon under extraction conditions favorable to selective extraction of the methanol, thereby providing a non-aqueous organic extract liquid stream rich in methanol and an aqueous raffinate stream containing unextracted methanol; charging liquid hydrocarbon extractant and extracted methanol substantially free of water to a first etherification catalytic reaction zone for contact with acid etherification catalyst under etherification process conditions for converting methanol and iso-alkene hydrocarbon to predominantly methyl tertiary-alkyl ether; fractionating the etherification effluent to recover liquid product containing methyl tertiary-alkyl ether; catalytically converting aqueous raffinate in contact with medium pore acid zeolite catalyst in a second methanol-to-gasoline (MTG) reaction zone concurrently with catalytic upgrading of unreacted methanol and olefinic overhead vapor to provide predominatly liquid $C_6^+$ hydrocarbon product along with $C_3$–$C_5$ alkane intermediate product, water, and light gas; separating water and light gas from MTG effluent to recover at least a fraction of $C_3$–$C_5$ alkane-rich intermediate and $C_6^+$ hydrocarbon product; dehydrogenating alkane intermediate to provide propene and olefinic hydrocarbon liquid rich in iso-alkenes; reacting propene from dehydrogenation with water to produce di-isopropyl ether; and recycling alkene-rich olefinic liquid as extraction solvent liquid for dewatering methanol feedstock.

Advantageously, unreacted alcohol and olefin vapor separated from etherification effluent may be converted along with aqueous alcoholic raffinate in a zeolite catalysis step to produce gasoline and paraffinic intermediate.

It is a further object of this invention to provide a novel reactor system configuration for achieving the process steps, including the fluid handling means for operatively connecting the unit operations described herein, with advantageous recycle of liquid olefins for use as an extraction solvent. These and other objects and features of the invention will be understood from the following description and in the drawing.

DRAWINGS

The single FIGURE of the drawing is a schematic process flowsheet depicting the present invention.

DETAILED DESCRIPTION

Typical feedstock materials for etherification reactions crude methanol commercially available from syngas processes, which may contain up to 30 wt % water, which must be removed, preferrably to a methanol purity of about 99.8 wt %. It has been found that more than 70% of crude feedstock methanol can be recovered by liquid extraction with light olefinic liquid extractant, such as butenes and $C_5^+$ light olefinic naphtha.

Referring to the drawing, a continuous stream of crude methanol (MeOH) feedstock is introduced via conduit 10 with a stream of olefinic hydrocarbon liquid extractant introduced via conduit 12 to extraction separation unit 14, preferably operated at about 35°–40° C. These streams are contacted under liquid extraction conditions to provide an aqueous raffinate phase. An aqueous stream containing a major amount of the water present in the crude feedstock is withdrawn via conduit 16.

The lighter organic extract phase containing hydrocarbon extraction solvent and the major amount of feedstock methanol is recovered from extraction unit 14 via conduit 18, and introduced under temperature and process conditions suitable for conversion of methanol in contact with etherification catalyst in reactor 20. Supplemental reactants, such as dry alcohol or isoalkenes may be added via line 19 to the etherification reaction zone to maintain stoichiometric ratio of reactants as desired. From reactor 20, the effluent stream 22 passes to a debutanizer fractionation tower 30.

In debutanizer separation unit 30 the $C_5^+$ tert-alkyl ether product (MTBE and/or TAME) is recovered as a liquid product stream 32, preferably along with unreacted $C_5$ hydrocarbons in the extractant. Fractionation tower overhead vapor comprising unreacted $C_4^-$ hydrocarbons and methanol is removed via conduit 34, and sent is sent to catalytic zeolite conversion unit 40, where it is contacted concurrently with aqueous raffinate from line 16. Optionally, fresh oxygenate feedstock, such as methanol or other C1-C4 alcohols, ethers, etc. may be added via line 10A directly to the MTG unit.

The aqueous raffinate stream 16 consists essentially of water, partitioned methanol (e.g.—50–80 wt. %), and a trace of hydrocarbon. This stream is reactive at elevated temperature in the presence of an acid zeolite catalyst, such as medium pore shape selective zeolite, such as, ZSM-5, etc., preferably in a fluidized bed MTG reaction zone to produce predominantly gasoline range liquid hydrocarbons, along with a saturated hydrocarbon intermediate to be treated as herein described. MTG effluent stream 42 is condensed and separated by phase and/or fractionation in unit 50 to provide a liquid gasoline product stream 52. Byproduct water is recovered in stream 53, along with light offgas 54, and a $C_3$–$C_5$ paraffinic intermediate hydrocarbon stream 56, rich in isobutane and isopentane.

Dehydrogenation unit 60 converts the intermediate hydrocarbons to an iso-alkene containing liquid suitable for use as an extraction solvent. The dehydrogenation may be achieved catalytically by known unit operations to produce a hydrogen byproduct gas and an olefinic product consisting essentially of $C_2$–$C_5$ olefins. All or a portion of the dehydrogenated aliphatics from unit 60 may be employed as extractant via line 12; however, it is within the inventive concept to separate a portion of these olefins for feeding to conversion unit 40 via line 12A. Paraffinic feed to the deydrogenation unit 60 may be supplemented via line 62 by various refinery streams containing propane and butanes, LPG or natural gas condensate.

The propene-rich $C_3$ stream 62 and a portion of byproduct water 53 from the MTG unit 40, or fresh makeup water, are contacted with an acid etherification catalyst in DIPE unit 70 to produce di-isopropyl ether, which may be recovered by conventional fractionation to provide product steam 72 and unreacted C3's 74. Byproduct isopropanol (IPA) may be recovered as product stream 76 or fed via line 34A to be converted in MTG unit 30 to produce additional hydrocarbons. Alternatively, IPA may be passed via line 19A as a reactant to primary ether reactor 14 to produce isopropyl t-butyl ether or the like. Unreacted propene recovered via line 73 may be removed from the system or optionally recycled along with IPA for further conversion in MTG unit 40.

Extraction Unit Operation

Although the alcohol feedstock may comprise one or more $C_1$–$C_4$ lower aliphatic alkanols, the preferred crude material is methanol containing about 2 to 20%, preferably 4 to 17% by weight water. Any suitable extraction equipment may be employed, including cocurrent, cross-current or single contactors, wherein the liquid methanol feedstock is intimately contacted with a substantially immiscible liquid hydrocarbon solvent, which may be a mixture of $C_4^+$ aliphatic components including lower alkanes, n-alkenes or relatively pure isoalkenes, such as isobutene (isobutylene). This unit operation is described in *Kirk-Othmer Encyclopedia of Chemical Technology* (Third Ed.), 1980, pp.672–721. Other equipment for extraction is disclosed in U.S. Pat. Nos. 4,349,415 (DeFilipi et al), 4,626,415 (Tabak), 4,665,237 (Arakawa et al) and 4,830,835 (Evers). Unit operation details are also disclosed by Harandi et al in U.S. Pat. Nos. 4,777,321 and 4,827,046, incorporated herein by reference. The methanol extraction step can be performed advantageously in a countercurrent multistage design, such as a simple packed column, rotating disk column, agitated column with baffles or mesh, or a series of single stage mixers and settlers. Typical methanol extraction with light olefins can be achieved in a liquid-liquid contact and separation unit operated at about 25°–65° C. (80°–150° F.).

Tertiary Ether Production

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977.

An article entitled "MTBE and TAME-A Good Octane Boosting Combo", by J.D. Chase, et al., *The Oil and Gas Journal*, Apr. 9, 1979, pages 149–152, discusses the technology. Preferred catalysts include polysulfonic acid resin, such as "Amberlyst 15" resin, Zeolite Beta or ZSM-5. Processes for producing and recovering MTBE and other methyl tert-alkyl ethers for $C_4$–$C_7$ isoolefins are known to those skilled in the art, such as disclosed in U.S. Pat. Nos. 4,544,776 (Osterburg et al) and 4,788,365 (Owen et al). Various suitable extraction and distillation techniques are known for recovering ether and hydrocarbon streams from etherication effluent.

MTG Conversion of Methanol to Hydrocarbons

The feedstock for a typical MTG process includes $C_1$–$C_4$ aliphatic alcohols and their ethers. It is known in the art to partially convert methanol by dehydration, as in the catalytic reaction over gamma-alumina to produce DME intermediate. This reaction can take place in direct conversion of methanol to gasoline (MTG). The MTG process unit may be a fixed bed type, as disclosed in U.S. Pat. Nos. 3,894,107; 3,928,483; 3,931,349; 4,048,250; etc. In a typical fixed-bed MTG process relatively large amounts of isobutane are produced, e.g., about 8%. In the past, it has been the practice to recover the isobutane fraction without an immediate upgrading step. In fluidized bed MTG operations, isobutane production may be optimized in the range of about 5–10 wt. % of hydrocarbon effluent.

Overall the producton of MTG gasoline plus ethers will increase blended gasoline pool octane because of their high component octanes. Alkene-containing gas from dehydrogenation can be routed directly or indirectly to the MTG unit to form additional gasoline.

The aqueous methanol raffinate stream may be co-reacted with olefinic light gas and/or other reactive hydrocarbon feedstreams in a conventional MTG reaction section, as described by Tabak in U.S. Pat. No. 4,654,453 and Owen et al in U.S. Pat. No. 4,788,365, incorporated herein by reference. The reaction severity conditions can be controlled to optimize yield of $C_3$–$C_5$ paraffins, olefinic gasoline or $C_6$–$C_8$ BTX hydrocarbons, according to product demand. MTG by-products include $C_4$ and $C_5$ iso-alkanes, which will ordinarily comprise at least 5% of the recovered product. It is understood that aromatic hydrocarbon and light paraffin production is promoted by those zeolite catalysts having a high concentration of Bronsted acid reaction sites. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

Upgrading of olefins by such hydrogen contributors in co-conversion reactors is taught by Owen et al in U.S. Pat. Nos. 4,788,365 and 4,090,949. In a typical process, the methanol and olefinic feedstreams are converted in a catalytic reactor under elevated temperature conditions and moderate pressure (i.e.—100 to 2500 kPa) to produce a predominantly liquid product consisting essentially of $C_6$+ hydrocarbons rich in paraffins and aromatics. The reaction temperature can be carefully controlled in the usual operating range of about 350° C. to 500° C.

Description of Zeolite Catalysts

Developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 1–250, preferably about 3 to 80 based on total catalyst weight. In the fluidized bed reactor the coked catalyst may have an apparent activity (alpha value) of about 3 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, and ZSM-48.

Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251, incorporated herein by reference.

While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity. Certain of the ZSM-5 type medium pore shape selective catalysts are sometimes known as pentasils. In addition to preferred aluminosilicates, the gallosilicate, and ferrosilicate materials may be employed. ZSM-5 type pentasil zeolites are particularly useful in the process because of their regenerability, long life and stability under the extreme conditions of operation. Usually the zeolite crystals have a crystal size from about 0.01 to 2 microns or more. It is advantageous to employ a standard ZSM-5 having a silica:alumina molar ratio of 25:1 or greater in a once-through MTG conversion unit to convert 60 to 100 percent, preferably at least 75 wt %, of the oxygenate and alkenes in a single pass.

A typical single pass reactor unit employs a temperature controlled in the usual operating range of about 250° C. to 650° C., preferably at average reactor temperature of 350° C. to 580° C., at moderate pressure of about 100 to 3000 kPa (atmospheric to about 400 psig). The weight hourly space velocity (WHSV, based on total alcohol in the feedstream) usually is about 0.1-5 WHSV.

Dehydrogenation Process Operation

An important unit operation in the conversion of iso-paraffins to their corresponding iso-olefins is dehydrogenation. Conventionally this can be achieved by high temperature cracking using hydrogenation-dehydrogenation catalyst; however, it is within the inventive concept to employ transhydrogenation in this process step to effect removal of hydrogen from the $C_3$–$C_5$ intermediate alkanes. Various processes are known for producing isoalkene-rich by dehydrogenation (including isomerization processes), such as discloses in U.S. Pat. No. 4,393,250 (Gottlieb et al). Typical processes are operated at elevated temperature (about 530°–700° C.) and moderate pressure using an active alumina solid catalyst impregnated with Pt or Cr oxide. Other dehydrogenation techniques are disclosed in *Oil & Gas Journal*, 8 Dec. 1980, pp 96–101; *Hydrocarbon Processing*, April 1982, pp 171–4; U.S. patent application Ser. No. 179,729, filed 11 Apr. 1988, and in U.S. Pat. No. 4,216,346 (Antos).

DIPE Reaction

Olefin hydration to provide ethers and alcohols is well known. Reaction of propene with water to produce DIPE and byproduct isopropyl alcohol (IPA) is an acid catalyzed process step, as described in U.S. Pat. Nos. 4,214,107; 4,499,313 and pending application Ser. No. 336,582 filed Apr. 10, 1989 by Bell et al. The preferred catalytic methods for making DIPE employ solid acid catalysts, such as zeolites Y, Beta and/or ZSM-5 aluminosilicate. DIPE etherification conditions may vary widely in choice of temperature, pressure and reaction time. The preferred method of Bell et al reacts propene with water in a fixed bed of zeolite Beta at about 90° to 200° C. and pressure of at least 4000 kPa. However, it is understood that the unit operations described herein can be conducted with any number of specific process steps within the skill of the art.

The present invention is particularly advantageous in the economic dewatering of crude methanol, thus avoiding expensive and energy-intensive prefractionation by distillation. By extracting methanol from the crude feedstock with olefinic hydrocarbon reactant liquid, substantial utilities and equipment savings are

We claim:

1. A continuous process for converting crude methanol to ether and gasoline comprising the steps of:
   (a) contacting a crude methanolic feedstock containing water with a liquid olefinic hydrocarbon extraction solvent stream rich in $C_4^+$ iso-alkene hydrocarbon under extraction conditions favorable to selective extraction of the methanol, thereby providing a non-aqueous organic extract liquid stream rich in methanol and an aqueous raffinate stream containing unextracted methanol;
   (b) charging liquid hydrocarbon extractant and extracted methanol substantially free of water to a first etherification catalytic reaction zone for contact with acid etherification catalyst under etherification process conditions for converting methanol and iso-alkene hydrocarbon to predominantly methyl tertiary-alkyl ether;
   (c) fractionating the etherification effluent from step (b) to recover a liquid product steam containing methyl tertiary-alkyl ether and a light stream unreacted methanol and olefin;
   (d) catalytically converting aqueous raffinate from step (a) in contact with medium pore acid zeolite catalyst in a second methanol-to-gasoline reaction zone concurrently with catalytic upgrading of unreacted methanol and olefin from step (c) to provide predominantly liquid $C_6^+$ hydrocarbon product along with $C_3$–$C_5$ alkane intermediate product, water, and light gas;
   (e) separating water and light gas from step (d) to recover $C_3$–$C_5$ alkane-rich intermediate and $C_6^+$ hydrocarbon product;
   (f) dehydrogenating at least a fraction of alkane intermediate from step (e) to provide propene and olefinic hydrocarbon liquid rich in iso-alkenes;
   (g) reacting propene from dehydrogenation step (f) with water to produce di-isopropyl ether; and
   (h) recycling alkene-rich olefinic liquid from step (f) to step (a) as extraction solvent liquid for dewatering methanol feedstock.

2. The process of claim 1 wherein the acid etherification catalyst comprises ion exchange resin, wherein the methanolic feedstock consists essentially of methanol and about 4 to 20 wt. % water, and wherein the extraction liquid comprises a major amount of $C_4$–$C_5$ tertiary-alkenes.

3. The process of claim 1 wherein additional methanol is introduced with extracted methanol in step (b) to provide a stoichiometric excess of methanol over iso-alkene.

4. The process of claim 1 wherein byproduct isopropanol is coproduced with di-isopropyl ether by reaction of propene with water; and wherein said isopropanol is converted to hydrocarbons concurrently with raffinate alcohol.

5. The process of claim 1 wherein byproduct isopropanol is coproduced with di-isopropyl ether by reaction of propene with water; and wherein at least a portion of said isopropanol is converted to t-alkyl ether by reaction with isobutylene or isoamylene.

6. The process of claim 1 wherein at least a portion of unconverted propene from step (g) is recovered and recycled to step (d) for further conversion.

7. The process of claim 1 wherein the methanol raffinate in step (d) is converted concurrently with fresh C1–C4 aliphatic oxygenate added to the methanol-to-gasoline reaction zone as supplemental feed.

8. A process for converting crude aqueous alcohol feedstock to gasoline and ether product comprising the steps of:
   contacting the aqueous alcohol feedstock with liquid hydrocarbon extractant comprising $C_4$–$C_5$ mixed olefinic hydrocarbons comprising isobutylene and isoamylenes under liquid extraction conditions;
   recovering an aqueous raffinate phase containing a portion of feedstock alcohol and a major amount of water introduced with the feedstock;
   recovering an organic extract phase comprising the hydrocarbon extractant and alcohol introduced in the feedstock;
   catalytically converting alcohol in the raffinate phase to predominantly gasoline range hydrocarbons and lower paraffinic hydrocarbons rich in $C_3$–$C_5$ alkane intermediates;
   dehydrogenating at least a portion of alkane intermediate from step (e) to provide propene and olefinic hydrocarbon liquid rich in isobutene; and
   reacting propene from dehydrogenation with water to produce di-isopropyl ether.

9. The process of claim 8 wherein t-alkyl ether catalyst consists essentially of sulfonic acid resin and the crude feedstock contains methanol, ethanol or isopropanol and about 2 to 20 wt % water.

10. The process of claim 8 wherein said isobutene produced by dehydrogenation is recovered in a $C_4$–$C_5$ liquid stream and employed as extractant solvent liquid for dewatering alcohol feedstock.

11. The process of claim 8 wherein byproduct isopropanol is coproduced with di-isopropyl ether by reaction of propene with water; and wherein said isopropanol is converted to hydrocarbons concurrently with raffinate alcohol.

12. The process of claim 8 wherein byproduct isopropanol is coproduced with di-isopropyl ether by reaction of propene with water; and wherein at least a portion of said isopropanol is converted to t-alkyl ether by reaction with isobutylene or isoamylene.

13. The process of claim 8 wherein byproduct isopropanol is coproduced with di-isopropyl ether by reaction of propene with water; and wherein said isopropanol, di-isopropyl ether and tertiary-alkyl ether are blended with liquid $C_6^+$ hydrocarbons to produce high octane gasoline product.

14. The process of claim 8 herein the liquid hydrocarbon extractant comprises $C_4$ mixed olefinic hydrocarbons comprising isobutene and n-butenes.

15. A continuous process for converting lower aliphatic alcohol to alkyl ether and gasoline comprising the steps of:
   reacting lower aliphatic alcohol with a liquid olefinic hydrocarbon stream rich in $C_4^+$ iso-alkene hydrocarbon in a first etherification catalytic reaction zone containing acid etherification catalyst under etherification process conditions for converting alcohol and iso-alkene hydrocarbon to predominantly tertiary-alkyl ether;

fractionating the etherification effluent to recover overhead stream containing unreacted alcohol and light olefinic hydrocarbon and to recover liquid product containing tertiary-alkyl ether;

catalytically converting unreacted alcohol and olefinic overhead stream from etherification concurrently with crude aqueous oxygenated hydrocarbon feedstock in contact with medium pore acid zeolite catalyst in a second catalytic reaction zone to provide predominantly liquid $C_6+$ hydrocarbon product along with $C_3$-$C_5$ alkane intermediate product, water, and light gas;

separating water and light gas from the second reaction zone to recover $C_3$-$C_5$ alkane-rich intermediate and $C_6+$ hydrocarbon product;

dehydrogenating alkane intermediate to provide propene and liquid olefinic hydrocarbon rich in $C_4+$ iso-alkenes;

reacting propene from dehydrogenation with water from alcohol conversion to produce di-isopropyl ether; and recycling said dehydrogenated olefinic liquid hydrocarbon directly or indirectly to the etherification reaction zone.

16. The process of claim 15 wherein the alkane intermediate includes at least 5% isobutane, based on total hydrocarbon effluent from the second reacton zone.

17. The process of claim 15 wherein the etherificaton catalyst comprises sulfonic acid resin and the medium pore zeolite comprises acid ZSM-5.

18. A continuous operatively-connected reactor system for converting crude lower alkyl alcohol to lower alkyl ethers comprising:
(a) extraction means for contacting crude aqueous alcohol feedstock containing with a liquid hydrocarbon extraction solvent rich in $C_4+$ iso-alkene hydrocarbon under extraction conditions favorable to selective extraction of the alcohol, thereby providing an extract liquid stream rich in alcohol and an aqueous raffinate stream lean in alcohol;
(b) first etherification reactor means operatively connected to receive the extract liquid stream for charging liquid hydrocarbon extractant and extracted methanol substantially free of water to a first catalytic reaction zone containing acid etherification catalyst for converting alcohol and iso-alkene hydrocarbon to predominantly lower alkyl t-alkyl ether;
(c) fractionation means for separating etherification effluent from reactor (b) to recover unreacted alcohol and light olefinic hydrocarbon overhead stream and to recover liquid product containing ether product;
(d) second catalytic reactor means for upgrading said aqueous raffinate stream from extraction means (a) for conversion of alcohol to hydrocarbons in reactor (d);
(e) means for separating water and light gas from the second reaction zone to recover $C_3$-$C_5$ alkane-rich intermediate and $C_6+$ hydrocarbon product;

third reactor means for dehydrogenating at least a fraction of alkane intermediate to provide propene and liquid olefinic hydrocarbon rich in $C_4+$ iso-alkenes;

fourth reactor means for reacting propene from dehydrogenation with water from alcohol conversion to produce di-isopropyl ether; and handling means for recycling said dehydrogenated olefinic liquid hydrocarbon directly or indirectly to the etherification reaction zone.

19. The reactor system of claim 18 wherein the acid etherification catalyst comprises ion exchange resin.

20. The reactor system of claim 18 the secondary reactor means contains acid medium pore zeolite catalyst and means for concurrently upgrading olefinic overhead stream from fractionator (c).

21. A catalytic reactor system for converting methanol-rich oxygenate feedstock to liquid hydrocarbons comprising:
zeolite catalysis reactor means for converting oxygenate feedstock predominantly to gasoline range hydrocarbons in a MTG reactor zone in contact with acid shape selective, medium pore zeolite catalyst thereby producing a minor amount of isobutane;

separation means for recovering a $C_6+$ gasoline product stream, a water stream and $C_3$-$C_5$ paraffinic intermediate hydrocarbon stream from the MTG reactor effluent;

dehydrogenation reactor means for converting said paraffinic intermediate stream predominantly to $C_3$-$C_5$ lower olefins comprising propene;

means for recovering a propene stream from dehydrogenation reactor effluent; and etherification reactor means for contacting said propene stream and said water stream in contact with etherificaton catalyst for conversion to isopropyl ether.

22. The system of claim 19 wherein catalyst in the MTG reactor zone comprises acid ZSM-5.

23. A continuous reactor system according to claim 19 for converting crude lower alkyl alcohol to lower alkyl t-alkyl ethers further comprising:
extraction means for contacting crude aqueous alcohol feedstock containing water with a liquid hydrocarbon extraction solvent rich in $C_4+$ iso-alkene hydrocarbon under extraction conditions favorable to selective extraction of the alcohol, thereby providing an extract liquid stream rich in alcohol and an aqueous raffinate stream lean in alcohol;

means for operatively connecting a tertiary etherification reactor to receive the extract liquid stream for contacting liquid hydrocarbon extractant and extracted alcohol substantially free of water with etherification catalyst for converting dewatered alcohol and iso-alkene hydrocarbon to predominantly lower alkyl t-alkyl ether; and means for charging at least a portion of said aqueous raffinate stream from the extractor means for conversion of alcohol to hydrocarbons concurrently with olefin upgrading in the MTG reactor zone.

* * * * *